(12) United States Patent
Rose et al.

(10) Patent No.: US 10,987,459 B2
(45) Date of Patent: Apr. 27, 2021

(54) METHOD AND SYSTEM FOR THE CALIBRATION OF DEVICES FOR IDENTIFYING BLOOD OR BLOOD CONSTITUENTS IN A FLUID

(71) Applicant: FRESENIUS MEDICAL CARE DEUTSCHLAND GMBH, Bad Homburg (DE)

(72) Inventors: Andreas Rose, Frankfurt am Main (DE); Sylvia Heinitz, Bamberg (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 0 days.

(21) Appl. No.: 16/485,470

(22) PCT Filed: Feb. 15, 2018

(86) PCT No.: PCT/EP2018/053797
§ 371 (c)(1),
(2) Date: Aug. 13, 2019

(87) PCT Pub. No.: WO2018/149921
PCT Pub. Date: Aug. 23, 2018

(65) Prior Publication Data
US 2019/0388601 A1    Dec. 26, 2019

(30) Foreign Application Priority Data

Feb. 16, 2017  (DE) .................. 10 2017 001 484.1

(51) Int. Cl.
*A61M 1/16* (2006.01)
*B01D 61/24* (2006.01)
(Continued)

(52) U.S. Cl.
CPC ......... *A61M 1/1692* (2013.01); *B01D 61/243* (2013.01); *G01D 18/00* (2013.01);
(Continued)

(58) Field of Classification Search
CPC .............. A61M 1/1692; A61M 1/3639; A61M 2205/15; A61M 2205/3313;
(Continued)

(56) References Cited

U.S. PATENT DOCUMENTS 3,512,895 A * 5/1970 Franc ................. G01N 21/4785
356/243.1
3,764,646 A * 10/1973 Hach ....................... B29C 39/12
264/162

(Continued)

FOREIGN PATENT DOCUMENTS

DE      2631686 A1    1/1977
DE      3423922 A1    1/1986
(Continued)

OTHER PUBLICATIONS

International Search Report and Written Opinion issued in corresponding International Patent Application No. PCT/EP2018/053797 (with English translation of International Search Report) dated Jun. 18, 2018 (22 pages).

(Continued)

*Primary Examiner* — Joseph W Drodge
(74) *Attorney, Agent, or Firm* — Kilyk & Bowersox, P.L.L.C.

(57) ABSTRACT

The invention relates to a method and to an assembly for calibrating devices 11 for detecting blood or blood components in a liquid, in particular dialysate, which devices comprise a light transmitter 17 and a light receiver 18, and an evaluation unit 20 that receives the signal from the light receiver 18 and is designed such that blood or blood components in the liquid are detected on the basis of the weakening of radiation passing through the liquid. The method according to the invention is based on the fact that the calibration of the devices 11 for detecting blood or blood components is carried out without the use of blood. The (Continued)

calibration is carried out using an absorption standard 30, which has predetermined optical properties in relation to the absorption of the light in blood, the absorption standard 30 being arranged in the beam path 19 between the light transmitter 17 and the light receiver 18. The absorption standard 30 makes it possible to identify defined spectral weakening in the light depending on the components of the blood, in particular haemoglobin. Since, by contrast with blood, the absorption standard 30 does not bring about any scattering, meaning that the beam path is influenced in a different way from blood, the calibration is also carried out using a scattering standard 36, which has predetermined optical properties in relation to the scattering of the light in blood. The assembly also comprises a beam deflection unit 22 for coupling out light for a spectral measurement of the light transmitter 17 using a spectrometer 27.

28 Claims, 4 Drawing Sheets (51) Int. Cl.
| | | |
|---|---|---|
| | *G01D 18/00* | (2006.01) |
| | *G01J 3/02* | (2006.01) |
| | *G01J 3/10* | (2006.01) |
| | *G01N 21/27* | (2006.01) |
| | *A61M 1/36* | (2006.01) |

(52) U.S. Cl.
CPC ........... *G01J 3/0275* (2013.01); *G01J 3/0291* (2013.01); *G01J 3/10* (2013.01); *G01N 21/274* (2013.01); *A61M 1/3639* (2013.01); *A61M 2205/15* (2013.01); *A61M 2205/3313* (2013.01); *A61M 2205/3331* (2013.01); *A61M 2205/70* (2013.01)

(58) Field of Classification Search
CPC ...... A61M 2205/3331; A61M 2205/70; A61M 2205/3306; A61M 2205/331; A61M 2205/705; A61M 1/16; A61M 1/1619; G01N 21/93; G01N 21/278; G01N 21/276; G01N 15/0205; G01N 15/0211; G01N 21/25; G01N 21/255; G01N 21/274; G01N 23/2076; G01J 3/00; G01J 3/02; G01J 3/027; G01J 3/0297; G01J 1/10; G01J 3/0275; G01J 3/0291; B01D 61/24; B01D 61/243; B01D 61/30; B01D 61/32; G01D 18/00; G01D 18/008
USPC ....... 210/94, 646, 745; 250/574; 356/39, 42, 356/300, 306, 319, 326, 451; 422/82.05; 436/164, 171
See application file for complete search history.

(56) References Cited

U.S. PATENT DOCUMENTS

| | | | |
|---|---|---|---|
| 4,181,610 A | | 1/1980 | Shintani et al. |
| 4,370,983 A * | | 2/1983 | Lichtenstein ............ A61B 5/00 600/301 |
| 4,417,355 A * | | 11/1983 | Anisovich .......... G01N 23/2076 378/49 |
| 4,707,131 A * | | 11/1987 | Schiek .................. G01N 21/51 250/574 |
| 5,354,725 A * | | 10/1994 | Eguchi .................. B41M 5/345 428/212 |
| 5,591,344 A | | 1/1997 | Kenley et al. |
| 5,601,080 A | | 2/1997 | Oppenheimer |
| 5,612,782 A * | | 3/1997 | Keranen ................ G01D 18/00 250/252.1 |
| 5,741,441 A * | | 4/1998 | Watts ................ G01N 21/4785 252/408.1 |
| 5,817,007 A * | | 10/1998 | Fodgaard ............. G01N 21/359 600/322 |
| 5,963,335 A * | | 10/1999 | Boutelle ................ G01N 21/59 356/39 |
| 6,064,474 A * | | 5/2000 | Lee ...................... G01N 21/314 356/39 |
| 6,117,099 A * | | 9/2000 | Steuer ................. A61M 1/3621 422/44 |
| 6,174,728 B1 | | 1/2001 | Ben-David et al. |
| 6,470,279 B1 | | 10/2002 | Samsoondar |
| 7,095,491 B2 * | | 8/2006 | Forstner ............. A61B 5/14551 356/39 |
| 7,236,812 B1 * | | 6/2007 | Ballerstadt .......... A61B 5/0066 422/82.05 |
| 7,422,693 B2 * | | 9/2008 | Carter .................... B04B 13/00 210/512.1 |
| 2005/0006296 A1 * | | 1/2005 | Sullivan ................ A61M 1/262 210/321.6 |
| 2005/0168737 A1 * | | 8/2005 | Bradshaw ............. G01N 21/31 356/319 |
| 2010/0234786 A1 * | | 9/2010 | Fulkerson ........... A61M 1/3659 604/4.01 |
| 2010/0243876 A1 * | | 9/2010 | Resch-Genger ..... G01N 21/278 250/252.1 |
| 2012/0154789 A1 | | 6/2012 | Barrett et al. |
| 2014/0098359 A1 * | | 4/2014 | Gross ................. A61B 5/14546 356/36 |
| 2015/0185242 A1 * | | 7/2015 | Mimura ........... G01N 35/00613 422/64 |
| 2015/0331293 A1 * | | 11/2015 | Sotzing ..................... C25B 3/00 359/273 |
| 2016/0058933 A1 | | 3/2016 | Ballantyne et al. |
| 2017/0227397 A1 * | | 8/2017 | Cafferty .................... G01J 3/28 |
| 2017/0350815 A1 * | | 12/2017 | Dumont ................ G01J 1/4204 |

FOREIGN PATENT DOCUMENTS

| | | |
|---|---|---|
| DE | 19605260 A1 | 11/1996 |
| DE | 102004006238 A1 | 8/2005 |

OTHER PUBLICATIONS

International Preliminary Report on Patentability issued in corresponding International Patent Application No. PCT/EP2018/053797 dated Aug. 29, 2019 (12 pages).

\* cited by examiner

METHOD AND SYSTEM FOR THE CALIBRATION OF DEVICES FOR IDENTIFYING BLOOD OR BLOOD CONSTITUENTS IN A FLUID

This application is a National Stage Application of PCT/EP2018/053797, filed Feb. 15, 2018, which claims priority to German Patent Application No. 10 2017 001 484.1, filed Feb. 16, 2017.

The invention relates to a method and to an assembly for calibrating devices for detecting blood or blood components in a liquid, in particular dialysate, which devices comprise a light transmitter and a light receiver, and an evaluation unit that receives the signal from the light receiver and is designed such that blood or blood components in the liquid are detected on the basis of the weakening of radiation passing through the liquid.

In order to protect the patient during dialysis, devices are used which can reliably detect the ingress of blood into the dialysate, which is possible should the membrane of the dialyser rupture. These devices are also referred to as blood leakage detectors.

DE 20 2013 011 936 U1 describes a device for detecting blood or blood components in a dialysate, which device comprises a light transmitter for transmitting light in a first wavelength range and for transmitting light in a second wavelength range, the wavelength of the light in the first and second wavelength range being adapted to the absorption properties of the blood or the blood component that are dependent on the wavelength such that the light passing through the liquid in the first wavelength range is absorbed more strongly than the light passing through the liquid in the second wavelength range. Furthermore, the device comprises a light receiver for receiving the light passing through the liquid, and an evaluation unit which is configured such that the presence of blood or a blood component in the liquid is concluded on the basis of the varying degree to which the light is absorbed in the first and second wavelength range.

The known devices for detecting blood or blood components have to be calibrated after manufacture. First, a zero adjustment on the basis of a dialysate or RO water is carried out. For this purpose, a cuvette filled with dialysate or RO water is placed into the beam path of the blood leakage detector between the light transmitter and the light receiver. Calibration then takes place using a calibration solution obtained from bovine blood. When used for the first time, the bovine blood is measured for its hematocrit and is diluted with dialysate in a predetermined mixing ratio. However, the use of bovine blood has proven to be problematic in practice. In addition, to being costly to procure, the instability over time of the blood solution is a significant drawback. Owing to temperature fluctuations, incident light radiation and physiological (degradation) processes, the optical properties of the blood solution can change even within one working day.

The problem addressed by the present invention is to provide a simplified method for calibrating devices for detecting blood or blood components in a liquid, in particular dialysate. Furthermore, another problem addressed by the present invention is to provide an assembly for calibrating devices for detecting blood or blood components in a liquid, in particular dialysate, which allows simple calibration.

These problems are solved according to the invention by the features of the independent claims. The dependent claims relate to preferred embodiments of the invention.

The method according to the invention is based on the fact that the calibration of the devices for detecting blood or blood components is carried out without the use of blood, which greatly simplifies the method. The calibration is not carried out using a blood-containing calibration solution, but using two different calibration standards that take into account the particular optical properties of blood.

In the method according to the invention, the calibration is carried out using an absorption standard, which has predetermined optical properties in relation to the absorption of the light in blood, the absorption standard being arranged in the beam path between the light transmitter and the light receiver.

The absorption standard makes it possible to identify a defined spectral weakening of the light depending on the components of the blood, in particular haemoglobin. Using the absorption standard, the beam path of the device can be influenced in a targeted manner in order to detect blood, in order for it to be possible to check whether the light receiver or the evaluation unit is capable of detecting and correctly interpreting the spectral weakening. However, by contrast with blood, the absorption standard does not bring about any scattering, meaning that the beam path is influenced in a different way from blood. Therefore, the absorption standard cannot be considered a replacement for blood.

Owing to manufacturing tolerances, scattering of the light in the blood, in particular by the erythrocytes, can negatively affect the detection of blood. The scattering effect of the erythrocytes leads to homogenisation of the beam path. If, however, the beam path is not made to conform with the specifications because component or assembly tolerances are not respected, a homogenising effect due to light scattering can bring about measurement errors. In this case, sufficient sensitivity of the device for detecting blood would not be ensured. Therefore, the calibration is not only carried out using an absorption standard, but also using a scattering standard, which has predetermined optical properties in relation to the scattering of the light in blood. Like the absorption standard, the scattering standard is arranged in the beam path between the light transmitter and the light receiver.

Since the absorption standard and the scattering standard do not contain blood, the problem of it being costly to procure and unstable over time does not arise. The calibration can be carried out at any time using the blood-free absorption standard and scattering standard, which are easy to handle.

The predetermined optical properties of the absorption standard and the scattering standard are intended to correspond to the optical properties of the blood, in particular of human blood, in terms of the absorption of light and in terms of the scattering of light, respectively. However, for the calibration, it is not necessary for the optical properties of the absorption standard and the scattering standard to be identical to those of the blood, and instead it is sufficient in practice for the absorption standard and the scattering standard to have similar optical properties. If the devices for detecting blood that are to be calibrated are based on the evaluation of the differing absorption of light in various wavelength ranges, the optical properties of the absorption standard and the scattering standard are intended to correspond to the optical properties of blood, at least in the relevant wavelength ranges. For example, the transmittance spectrum of the absorption standard is intended to correspond to the transmittance spectrum of blood for at least two wavelength ranges, one wavelength range being between 550 nm and 575 nm and the other wavelength range being between 630 and 780 nm. In this context, the predetermined optical properties in relation to absorption and scattering are understood to be the optical properties of blood. The relevant optical properties of the absorption standard and scattering standard used can be determined using known measurement methods, and it can subsequently be checked whether these properties are sufficiently consistent with those of the blood.

In a device for detecting blood or blood components, the spectral distribution of the light from the light transmitter also influences the precision of the blood detection. The method according to the invention therefore provides a measurement of the spectral distribution of the light from the light transmitter. In particular, the method according to the invention provides a measurement of the spectrum in the wavelength ranges used.

During the calibration, a calibration data set is preferably determined that describes the characteristic properties of the device for detecting blood or blood components. The calibration data set may for example contain correction data, which is taken into account when evaluating the signal from the light receiver. The correction data may be correction factors, for example. The calibration data set may also contain data describing the spectral distribution of the light from the light transmitter. In addition, the calibration data set contains additional data for identifying the calibrated device for identifying blood or blood components, and therefore the determined calibration data sets can be assigned to the individual devices for detecting blood.

The determined calibration data sets are preferably stored in a storage medium of the device for detecting blood or blood components, or in a storage medium of a central storage apparatus, for example in the storage medium of a server. If the calibration data sets are stored in the storage medium of a server on the test bed, the data can be read out via a suitable interface at a later point in time. The identification data may be a serial number or a MAC address, for example.

The absorption standard comprises an absorption body that preferably has two parallel surfaces, such that the light can enter through one surface and exit from the other surface. If a plane-parallel colour filter is used, this needs to be precisely positioned and oriented in the beam path, and this can be achieved by suitable design measures, for example by a suitable filter holder.

A preferred embodiment of the absorption standard provides that the absorption body be a transparent casting compound in which a dye is embedded. Since the dye particles are encased in a casting compound, the dye particles can be distributed in a stable and homogenous manner. Embedding the dye in the casting compound makes it possible to reproducibly manufacture an absorption body that has predetermined optical properties and is characterised by a high long-term stability.

In tests, polymethyl methacrylate (PMMA) has proven to be particularly advantageous as a casting compound. In order to produce the plane-parallel colour filter, the dye is dissolved in a liquid casting compound, in particular PMMA, and the solution is cured in the form of a body having two parallel surfaces, for example in the form of a planar round or rectangular plate. However, it is also possible to cut a body having two parallel surfaces from a cured block. The surfaces of the absorption body may be treated using suitable processes, for example they may be ground or polished, in order to produce smooth surfaces.

The optical properties of the dye are intended to substantially correspond to the optical properties of the blood. The transmittance spectrum of the dye is intended to correspond to the transmittance spectrum of blood at least for the wavelength ranges used, in particular two wavelength ranges, one wavelength range being between 550 nm and 575 nm and the other wavelength range being between 630 and 780 nm.

Tests have shown that the dye from Lanxess Deutschland GmbH known by the trade name MACROLEX© RED VIOLET R is particularly suitable. Although the transmittance spectrum of this dye is not identical to the transmittance spectrum of blood, the optical properties in the wavelength ranges that are relevant here are consistent with the optical properties of blood to the extent that the dye can be used for the spectral weakening.

Another preferred embodiment of the absorption standard provides that the transparent casting compound be encapsulated between two parallel glass panes, which produces an optically homogenous light path through the glass panes and the casting compound.

Another preferred embodiment of the absorption standard comprises a cuvette filled with a liquid in which the absorption body is arranged. The cuvette is preferably a glass cuvette, in particular a cylindrical glass cuvette.

The cuvette can be filled with dialysate, which is characterised by being optically transparent and colourless. However, the dialysate is not stable in the long term. Therefore, a particularly preferred embodiment provides filling said cuvette with water which has been prepared using a reverse osmosis purification process (RO water). By adding polyethylene glycol (PEG), the risk of germs forming in the RO water can be further reduced, meaning that the long-term stability can be further increased. Filling the cuvette with RO water also has the advantage that the refractive index between the transition from the cuvette to the absorption body of the absorption standard is adjusted to the calibration standard for the zero adjustment of the device for detecting blood, which is likewise preferably filled with RO water but does not contain the absorption body.

A preferred embodiment of the scattering standard provides a scattering body that is matt or roughened on one side. The scattering body may be a rectangular or round plate, for example. The plate is preferably a glass plate. The plate may be rendered matt by suitable processing. For example, the surface of the plate may be sand-blasted or etched. The matt side of the plate may be provided with a seal made of a transparent lacquer or a transparent coating, such that the optical properties cannot be changed by a liquid into which the plate may be placed. The coating is preferably a layer of epoxy resin.

A particularly preferred embodiment of the scattering standard, which is characterised by an improved measuring effect, provides that the scattering standard have a scattering body that comprises two plates, of which one plate is matt or roughened on one side, the two plates being arranged on one another such that the matt or roughened side of said one plate is on the inside. An alternative particularly preferred embodiment provides a scattering body that comprises two plates which are matt or roughened on one side, the two plates being arranged on one another such that the matt sides of the two plates are on the inside. The two plates can be bonded to one another. In these embodiments too, the matt or roughened side of said one plate or the matt or roughened sides of the two plates cannot come into contact with a liquid.

The scattering standard may also comprise a scattering body made of a transparent casting compound in which scattering particles, in particular insoluble salts, polystyrene particles or gypsum, are embedded.

Like the absorption standard, the scattering standard comprises a cuvette filled with a liquid, preferably dialysate or RO water, in which the scattering body is arranged. Like the cuvette of the absorption standard, the cuvette of the scattering standard is inserted into the beam path between the light transmitter and the light receiver of the device for detecting blood.

In an alternative embodiment, which does not provide a solid scattering body, the scattering standard comprises a cuvette filled with a liquid containing a scattering particle. The cuvette is preferably filled with lipids dissolved in a liquid. The cuvette may for example be filled with the parenteral nutritional solutions from Fresenius Kabi AG known by the trade names Smoflipid or Intralipid.

However, it is also possible to produce a scattering body by introducing liquids containing a scattering particle into a space between two transparent plates, in particular glass plates, the space being sealed from the outside. This scattering body can in turn be inserted into the beam path of the device for detecting blood or blood components in a cuvette filled with a liquid, in particular dialysate or RO water.

In order to measure the spectral distribution of the light, preferably a beam deflection unit, in particular a deflection mirror, is arranged in the beam path between the light transmitter and the light receiver. The deflection mirror can deflect the light by 45°, such that the light can be easily coupled into a spectrometer. The reflectance of the mirror is ideally intended to be consistent and as high as possible in the relevant wavelength range of approximately 350 nm to 800 nm, such that little light is lost due to reflection.

The assembly according to the invention is intended for calibrating devices for detecting blood or blood components in a liquid, which devices comprise a holder for a cuvette that is designed such that a cuvette inserted into the holder is arranged in the beam path between the light transmitter and the light receiver.

The assembly according to the invention comprises an absorption standard that can be inserted into the holder for the cuvette and has predetermined optical properties in relation to the absorption of the light in blood, and a scattering standard that can be inserted into the holder for the cuvette and has predetermined optical properties in relation to the scattering of the light in blood. In addition, the assembly comprises an evaluation unit for determining a calibration data set that describes characteristic properties of the device for detecting blood or blood components, which calibration data set contains data for identifying the device for detecting blood or blood components. The assembly may also comprise a spectrometer for measuring the spectral distribution of the light from the light transmitter of the device for detecting blood or blood components.

The invention will be explained in more detail in the following with reference to the drawings, in which.

Figure 1:
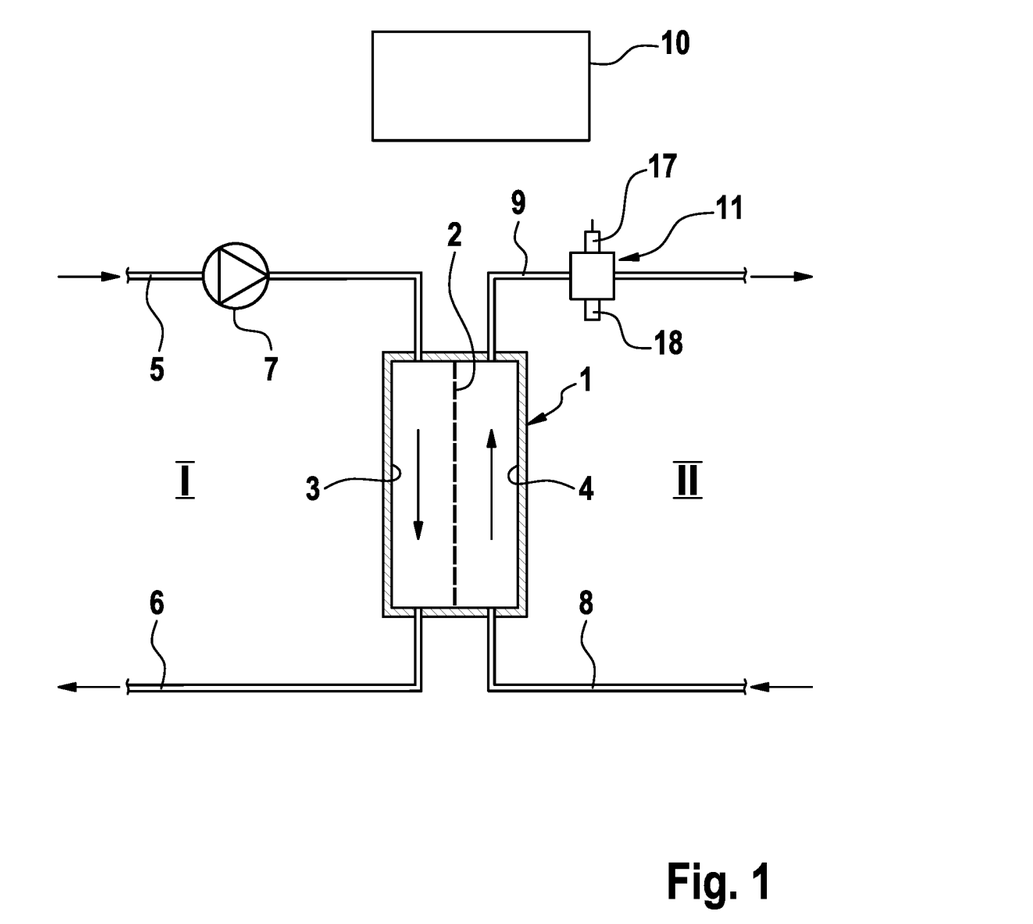
FIG. 1 is a simplified schematic view of a device for extracorporeal blood treatment which comprises a device for detecting blood or a blood component in the dialysate.

FIG. 1 is a highly simplified schematic view of a device for extracorporeal blood treatment, for example a dialysis device. The extracorporeal blood treatment device comprises a dialyser or a filter 1, which is divided into a blood chamber 3 and a dialysate chamber 4 by means of a semi-permeable membrane 2. An arterial blood line 5 leads from the patient to the blood chamber 3, while a venous blood line 6 leads away from the blood chamber 3 to the patient. A blood pump 7 arranged in the arterial blood line 5 conveys the blood in the extracorporeal blood circuit I. The dialysate branch II of the dialysis device is only shown in outline. The dialysate branch II comprises a dialysate supply line 8 that leads to the dialysate chamber 4, and a dialysate removal line 9 that leads away from the dialysate chamber 4. Furthermore, the blood treatment device comprises a central control unit 10 which controls the individual components, for example the blood pump 7.

If the membrane 2 of the dialyser 1 were to rupture, the patient's blood could enter the dialysate. Therefore, the blood treatment device has a device 11 for detecting blood or a blood component, in particular haemoglobin, in the dialysate.

Figure 2:
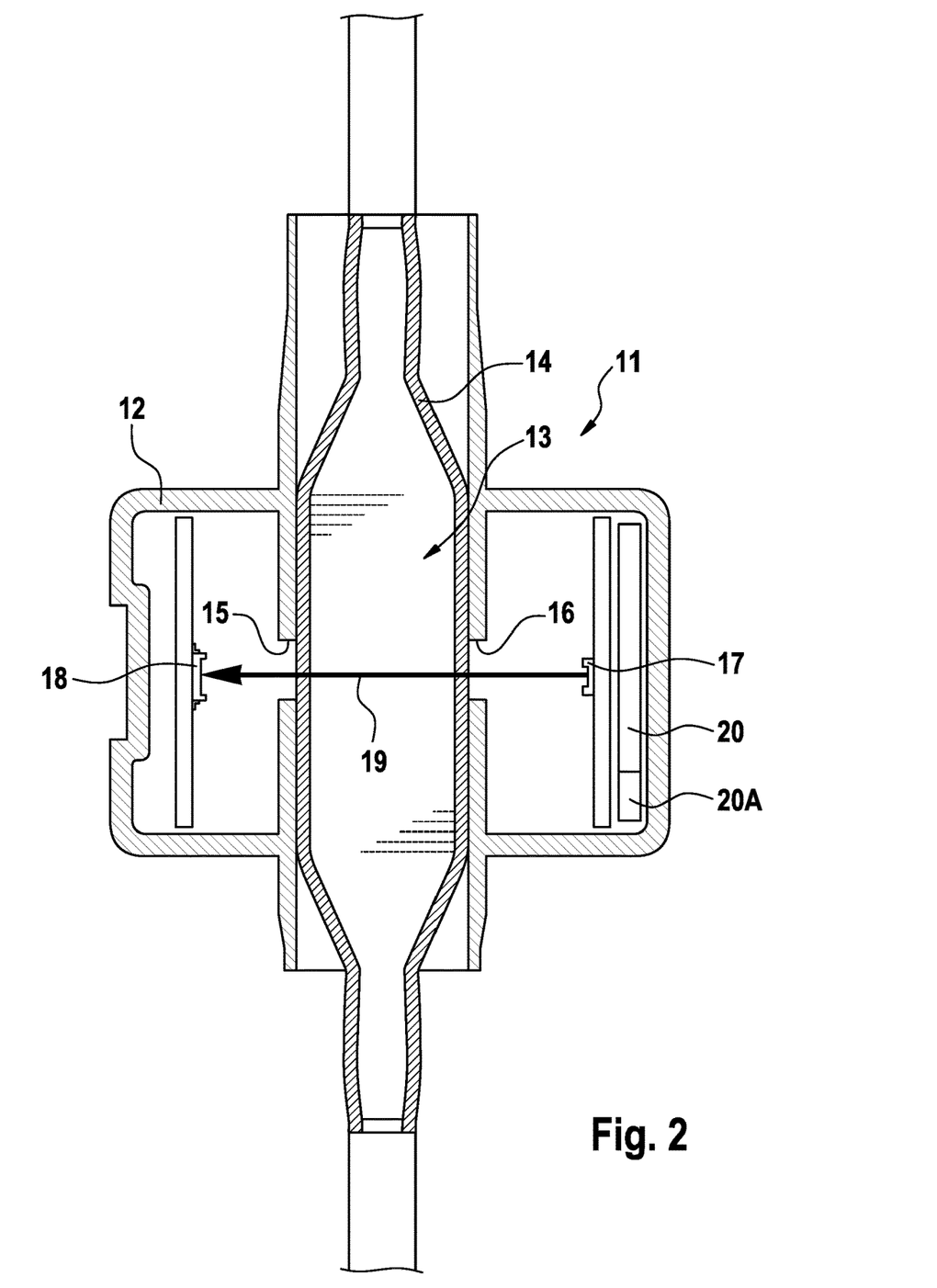
FIG. 2 is a sectional view of the device for detecting blood or a blood component, a cuvette being placed into the beam path.

FIG. 2 shows the essential components of the device 11 for detecting blood or a blood component. The device comprises a housing body 12 having a holder 13, into which a cuvette 14 can be fitted.

The holder 13 for the cuvette 14 has a first aperture diaphragm 15 and a second aperture diaphragm 16. A light transmitter 17 is arranged in front of one of the two aperture diaphragms 16 and a light receiver 18 is arranged in front of the other aperture diaphragm 17, such that the beam path 19 passes through one aperture diaphragm 16, enters the cuvette 14, leaves the cuvette, passes through the other aperture diaphragm 15 and impinges on the light receiver 18. The cuvette is a component of the dialysate removal line 9, and therefore dialysate flows through the cuvette.

The light transmitter 17, for example a bicolour LED, alternately emits green light having a wavelength of between 550 nm and 575 nm, preferably between 555 nm and 570 nm, particularly preferably between 560 nm and 565 nm, and red light or light that reaches the near-infrared range (NIR) that has a wavelength of between 630 nm and 780 nm, preferably between 630 nm and 675 nm, particularly preferably between 640 nm and 660 nm. The light receiver 18 generates an output signal that is proportional to the intensity of the received light. An evaluation unit 20 is provided for evaluating the signal from the light receiver, and is only shown schematically in FIG. 2.

The relationship between the intensity $I_0$, $I_1$ of the radiated and transmitted light describes the following equation (Beer-Lambert law):

$$lg(I_1/I_0) = -\alpha c d,$$

where $\alpha$ is the absorption coefficient, c is the concentration of the liquid, and d is the internal diameter of the cuvette.

The evaluation unit 20 receives the output signals from the light receiver 18 that are proportional to the intensity of the light and compares the intensity of the light in the first wavelength range and the intensity of the light in the second wavelength range with one another. The ingress of blood or a blood component, in particular haemoglobin, into the dialysate is concluded on the basis of the comparison of the measured intensities of the light. In order to evaluate the measurement signals, characteristic limit values can be specified. A method described in DE 37 26 524 A1 can be used for the evaluation, for example.

When evaluating the measured values, the evaluation unit 20 takes into account data contained in a calibration data set, which may include the spectral distribution of the light from the light transmitter 17 or correction factors determined during calibration. The calibration data set is stored in a storage medium 20A of the evaluation unit 20.

In the following, the assembly for the blood-free calibration of the device 11 for detecting blood or blood components is described.

Various measurements are taken for the calibration, the measured values being evaluated using an evaluation unit 21 that determines a calibration data set which describes the characteristic properties of the device 11 for detecting blood or blood components that are determined during calibration. For identifying the device for detecting blood or blood components, the calibration data set contains additional data, for example a serial number or a MAC address. The calibration data set can be input into the storage medium 20A of the evaluation unit 20 of the device 11 for detecting blood or blood components via a data line (not shown), such that the measured values can be evaluated in order to detect blood or blood components on the basis of the calibration data set. Alternatively, the calibration data set can also be stored in the storage medium of a central storage device (server) (not shown), from which the data can then be input into the evaluation unit 20 of the device 11 for detecting blood or blood components or into a storage medium of the central control unit 10 of the blood treatment device, such that the evaluation unit 20 can access the data.

Prepared cuvettes are used for the calibration which are inserted into the holder 13 of the device 11 for detecting blood or blood components, in order for it to be possible to take various measurements. The calibration is carried out in individual calibration zones, which are traversed in succession. The individual measurements are taken in the calibration zones, the measured values being evaluated in the unit 21 for evaluating the calibration status.

Figure 3:
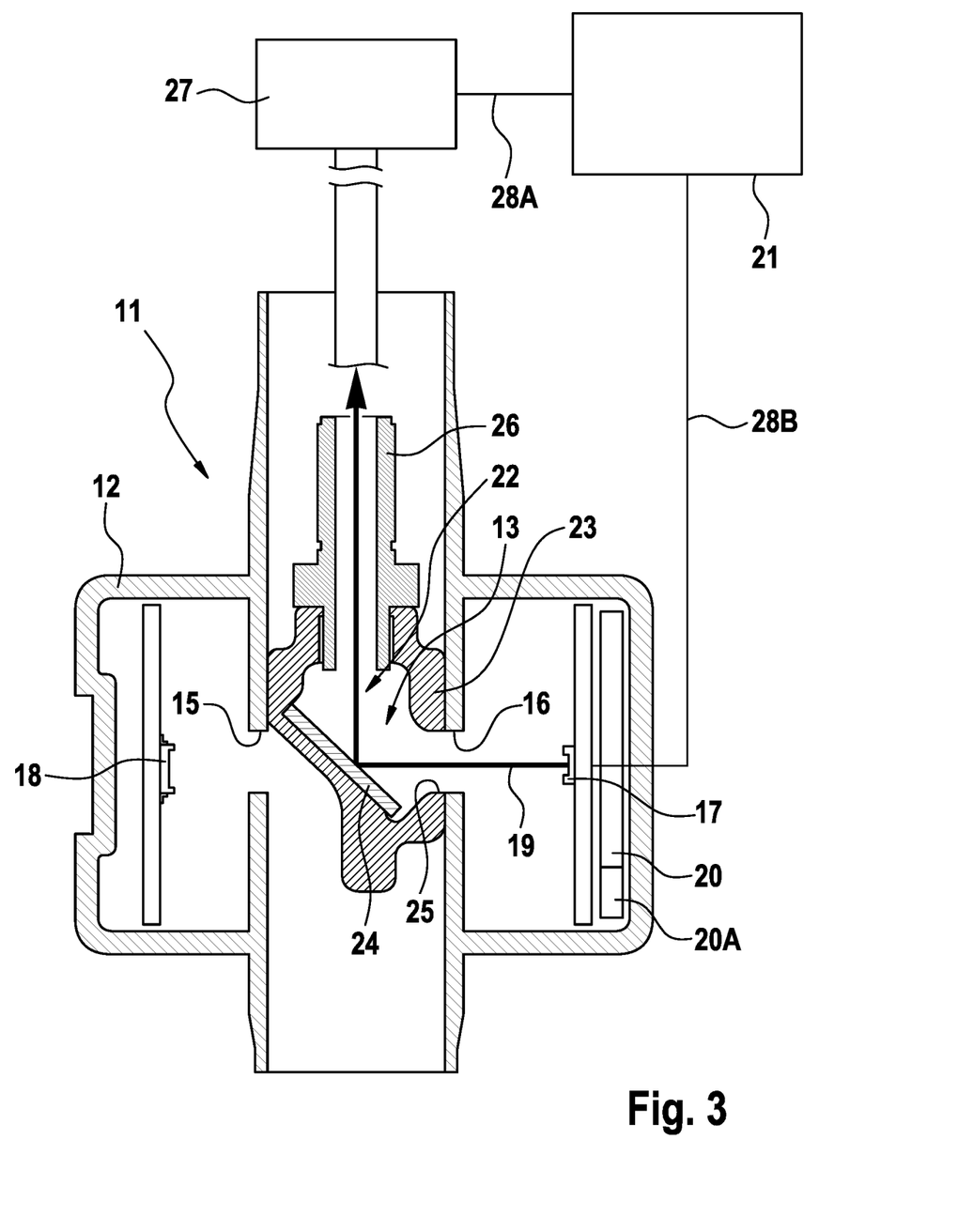
FIG. 3 is a sectional view of the device for detecting blood or a blood component, a beam deflection unit being placed into the beam path.

In the first calibration zone, the spectrum of the light transmitter 17 of the device 11 for detecting blood or blood components, in particular the spectrum of the green and red light, is measured. For the measurement, instead of a cuvette, a beam deflection unit 22 is fitted into the holder 13 of the device 11 for detecting blood or blood components. FIG. 3 shows the device 11 for detecting blood or blood components together with the beam deflection unit 22.

The beam deflection unit 22 comprises a housing body 23 in which a deflection mirror 24 is arranged, which encloses an angle of 45° together with the beam path 19. Rather than a mirror, a prism may equally well be arranged in the beam path. In the beam path 19, an aperture diaphragm 25 is positioned in front of the mirror 24, and in one embodiment a cosine corrector 26 is positioned behind the mirror, by means of which the light is coupled into a spectrometer 27 connected to the evaluation unit 22 via a data line 28A. The spectral measurement is used to assess the position of the spectra in relation to the absorption of haemoglobin.

A zero adjustment on the basis of RO water takes place in the second calibration zone, and PEG is preferably added to this water (1% PEG solution). In this step, the intensity of the light from the light transmitter 17 can be measured. For the zero adjustment, a cuvette filled with RO water is inserted into the beam path of the device for detecting blood or blood components between the light transmitter 17 and the light receiver 18, such that the light from the light transmitter can pass through the cuvette and impinge on the light receiver. The output signal from the light receiver 18 is evaluated using the unit 21 for evaluating the calibration status. The evaluation unit receives the signal from the light receiver 18 via a data line 28B.

Figure 4:
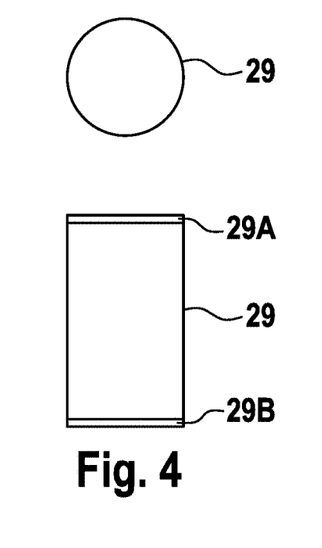
FIG. 4 is a simplified view of a cuvette for a zero adjustment.

FIG. 4 is a side view and a plan view of the cylindrical glass cuvette 29 for the zero adjustment, which is sealed on the top and bottom by a sealing part 29A, 29B.

The absorption is measured in the third calibration zone using an absorption standard in order to check whether a specified output signal is generated for predetermined spectral weakening. For the absorption measurement, the absorption standard is inserted into the holder 13 of the device 11 for detecting blood or blood components, such that the light from the light transmitter 17 can pass through the absorption standard and impinge on the light receiver 18. The output signal from the light receiver 18 is evaluated in the evaluation unit 21.

Figure 5:
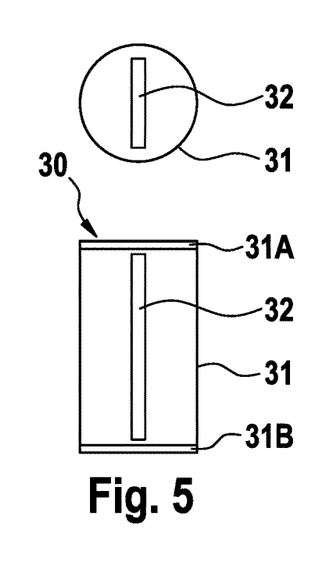
FIG. 5 is a simplified view of an absorption standard.

FIG. 5 shows the absorption standard 30, which comprises a cylindrical glass cuvette 31, which is sealed on the top and bottom by a sealing part 31A, 31B. The glass cuvette 31 is filled with RO water or a solution of RO water and PEG. An absorption body 32 is arranged in the cuvette. The two sealing parts 31A, 31B are designed as a mount for the absorption body 32.

Figure 5A:
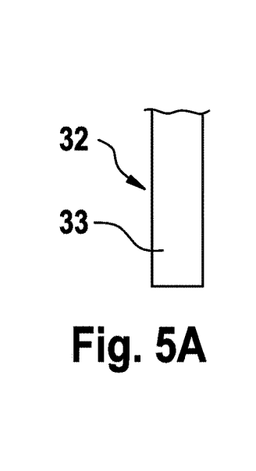
FIG. 5A is a simplified view of a first embodiment of an absorption body of the absorption standard.
Figure 5B:
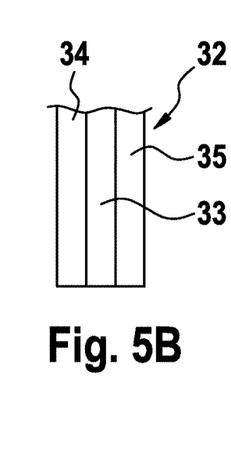
FIG. 5B is a simplified view of a second embodiment of an absorption body of the absorption standard.

FIG. 5A shows a first embodiment of the absorption body 32. In this embodiment, the absorption body is a plate 33 that has polished surfaces and is made of a casting compound which contains a homogenous distribution of the dye MAC-ROLEX© Red Violet R. The casting compound is polymethyl methacrylate (PMMA). The plate may be cut from a block, or the casting compound may be cast in the form of a plate. FIG. 5B shows an alternative embodiment in which the plate 33 is encapsulated between two parallel glass panes 34, 35.

In the fourth calibration zone, the scattering effect of blood is imitated using a scattering standard which, instead of the absorption standard 30, is inserted into the holder 13 of the device 11 for detecting blood or blood components. The output signal from the light receiver 18 is again evaluated by the evaluation unit 21.

Figure 6:
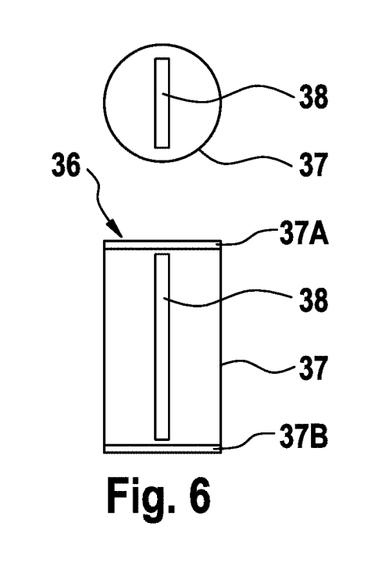
FIG. 6 is a simplified view of a scattering standard.

FIG. 6 shows the scattering standard 36, which comprises a cylindrical glass cuvette 37, which is sealed on the top and bottom by a sealing part 37A, 37B and in which a scattering body 38 is arranged. The two sealing parts 37A, 37B are designed as a mount for the scattering body 38. The cuvette 37 is filled with RO water or a solution of RO water and PEG.

Figure 6A:
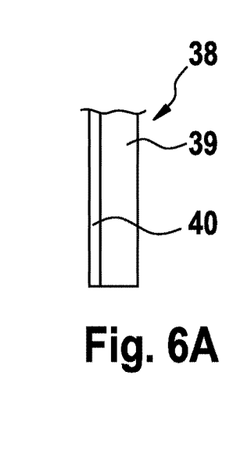
FIG. 6A is a simplified view of a first embodiment of a scattering body of the scattering standard.
Figure 6B:
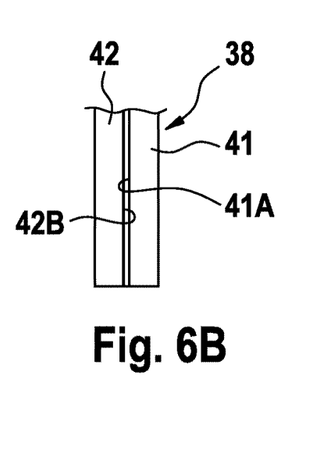
FIG. 6B is a simplified view of a second embodiment of a scattering body of the scattering standard.

FIG. 6A shows a first embodiment of the scattering body 38. In this embodiment, the scattering body 38 is a glass plate 39 that is matt or roughened on one side 40. FIG. 6B shows an alternative embodiment of the scattering body 38, which comprises two glass plates 41, 42 that are bonded to one another. The two glass plates 41, 42 are matt or roughened on the inner faces 41A, 42B. It is however possible for the inner face of just one of the two glass plates to be matt or roughened.

However, like the absorption body, the scattering body may also be made of a transparent casting compound, to which, instead of a dye, scattering particles are added such that they are homogenously distributed. The scattering particles may be insoluble salts, polystyrene particles, titanium dioxide or gypsum.

Figure 7:
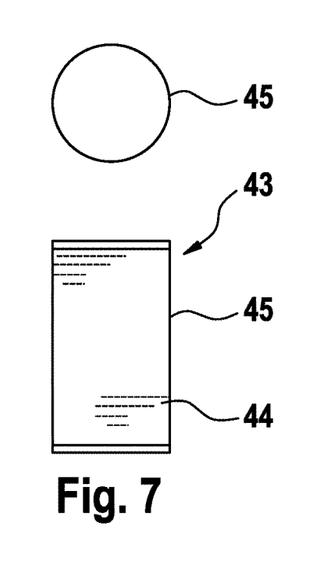
FIG. 7 is a simplified view of another embodiment of a scattering standard.

FIG. 7 shows an embodiment of a scattering standard 43 that contains a scattering liquid 44 instead of a scattering body. The scattering liquid is a lipid-containing solution, for example. The parenteral nutritional solutions from Fresenius Kabi AG known by the trade names Smoflipid or Intralipid may be used, for example. The scattering standard 44 comprises a cuvette 45 filled with a scattering liquid 44.

The invention claimed is:

1. A method for calibrating a device for detecting blood or blood components in a liquid in a dialysate line, the device comprising a light transmitter, a light receiver, and an evaluation unit that receives a signal from the light receiver and is designed such that blood or blood components in the liquid in the dialysate line are detected on a basis of an intensity of radiation passing through the liquid in the dialysate line,
   wherein the calibrating of the device for detecting blood or blood components occurs without exposure of the device to a blood-containing calibration solution, the calibrating uses an absorption standard and a scattering standard, the absorption standard has predetermined optical properties in relation to an absorption of light in blood, the absorption standard is arranged in a beam path between the light transmitter and the light receiver, the scattering standard has predetermined optical properties in relation to a scattering of the light in blood, and the scattering standard is arranged in the beam path between the light transmitter and the light receiver.

2. The method according to claim 1, wherein a spectral distribution of light from the light transmitter is measured.

3. The method according to claim 1, wherein a calibration data set is determined that describes characteristic properties of the device for detecting blood or blood components, and the calibration data set contains data for identifying the device for detecting blood or blood components.

4. The method according to claim 3, wherein the calibration data set is stored in a storage medium of the device for detecting blood or blood components, or in a central storage apparatus.

5. The method according to claim 1, wherein the absorption standard comprises an absorption body that has two parallel surfaces and is made of a transparent casting compound, in which a dye is embedded.

6. The method according to claim 5, wherein the transparent casting compound is encapsulated between two parallel glass panes.

7. The method according to claim 5, wherein the absorption standard comprises a cuvette filled with a liquid, and the absorption body is arranged in the cuvette.

8. The method according to claim 5, wherein a transmittance spectrum of the dye corresponds to a transmittance spectrum of blood for at least two wavelength ranges, one wavelength range being between 550 nm and 575 nm and the other another wavelength range being between 630 nm and 780 nm.

9. The method according to claim 5, wherein the dye is MACROLEX© Red Violet R.

10. The method according to claim 1, wherein the scattering standard comprises a scattering body having a plate that is matt or roughened on one side.

11. The method according to claim 10, wherein a matt side of the plate is provided with a seal made of a transparent lacquer or a transparent coating.

12. The method according to claim 10, wherein the scattering standard comprises a cuvette filled with a liquid, and the scattering body is arranged in the cuvette.

13. The method according to claim 1, wherein the scattering standard has a scattering body that comprises two plates, of which one plate has a matt side on one side, the two plates being arranged on one another such that the matt side of the one plate is on an inside of the arrangement facing a second a side of the one plate facing the other plate of the two plates, or the scattering standard has a scattering body that comprises two plates, each of which has a matt side on one side, the two plates being arranged on one another such that the matt sides of the two plates are on an inside of the arrangement respective sides of the two plates facing each other.

14. The method according to claim 1, wherein the scattering standard comprises a scattering body made of a transparent casting compound in which scattering particles are embedded.

15. The method according to claim 1, wherein the scattering standard comprises a cuvette filled with a liquid containing a scattering particle.

16. The method according to claim 1, wherein, in order to measure a spectral distribution of the light, a beam deflection unit is arranged in the beam path between the light transmitter and the light receiver, light deflected by the beam deflection unit being coupled into a spectrometer.

17. An assembly for calibrating a device for detecting blood or blood components in a liquid in a dialysate line, the device comprising a light transmitter, a light receiver, and an evaluation unit that receives a signal from the light receiver and is designed such that blood or blood components in the liquid in the dialysate line are detected on the basis of an intensity of radiation passing through the liquid in the dialysate line, the device for detecting blood or blood components comprising a holder for a cuvette, which is designed such that a cuvette inserted into the holder is arranged in a beam path between the light transmitter and the light receiver,
   wherein the assembly comprises:
   an absorption standard that inserts into the holder for the cuvette and has predetermined optical properties in relation to an absorption of light in blood,
   a scattering standard that inserts into the holder for the cuvette and has predetermined optical properties in relation to a scattering of the light in blood, and
   a second evaluation unit for determining a calibration data set that describes characteristic properties of the device for detecting blood or blood components, the calibration data set containing data for identifying the device for detecting blood or blood components.

18. The assembly according to claim 17, wherein the assembly comprises a spectrometer for measuring a spectral distribution of light from the light transmitter of the device for detecting blood or blood components.

19. The assembly according to claim 17, wherein the absorption standard comprises an absorption body that has two parallel surfaces and is made of a transparent casting compound, in which a dye is embedded.

20. The assembly according to claim 19, wherein the transparent casting compound is encapsulated between two parallel glass panes.

21. The assembly according to claim 19, wherein a transmittance spectrum of the dye corresponds to a transmittance spectrum of blood for at least two wavelength ranges, one wavelength range being between 550 nm and 575 nm and the other another wavelength range being between 630 nm and 780 nm.

22. The assembly according to claim 17, wherein the absorption standard comprises a cuvette that is filled with a liquid and inserted into the holder, the absorption body being arranged in the cuvette.

23. The assembly according to claim 17, wherein the scattering standard comprises a scattering body having a plate that is matt on one side.

24. The assembly according to claim 23, wherein the scattering standard comprises a cuvette that is filled with a liquid and inserted into the holder, the scattering body being arranged in the cuvette.

25. The assembly according to claim 17, wherein the scattering standard has a scattering body that comprises two plates, of which one plate has a matt side on one side, the two plates being arranged on one another such that the matt side is on an inside of the arrangement facing a second a side of the one plate facing the other plate of the two plates, or the scattering standard has a scattering body that comprises two plates, each of which has a matt side on one side, the two plates being arranged on one another such that the matt sides of the two plates are on an inside of the arrangement respective sides of the two plates facing each other.

26. The assembly according to claim 17, wherein the scattering standard comprises a scattering body made of a transparent casting compound in which scattering particles are embedded.

27. The assembly according to claim 17, wherein the scattering standard comprises a cuvette filled with a liquid containing a scattering particle.

28. The assembly according to claim 17, wherein, in order to measure a spectral distribution of the light, a beam deflection unit is arranged in the beam path between the light transmitter and the light receiver.

* * * * *

UNITED STATES PATENT AND TRADEMARK OFFICE
CERTIFICATE OF CORRECTION

PATENT NO. : 10,987,459 B2  
APPLICATION NO. : 16/485470  
DATED : April 27, 2021  
INVENTOR(S) : Rose et al.

Page 1 of 1

It is certified that error appears in the above-identified patent and that said Letters Patent is hereby corrected as shown below:

In the Claims

In Claim 8, at Column 9, Line 58, delete "the other".

In Claim 13, at Column 10, Lines 8-9, delete "an inside of the arrangement facing a second"; and at Lines 13-14, delete "an inside of the arrangement".

In Claim 25, at Column 11, Line 18, delete "an inside of the arrangement facing a second"; and at Column 12, Line 5, delete "an inside of the arrangement".

Signed and Sealed this  
Tenth Day of August, 2021

Drew Hirshfeld  
*Performing the Functions and Duties of the*  
*Under Secretary of Commerce for Intellectual Property and*  
*Director of the United States Patent and Trademark Office*